United States Patent
Doi et al.

(10) Patent No.: US 8,344,166 B2
(45) Date of Patent: Jan. 1, 2013

(54) METHOD OF RETAINING THE QUALITY OF 2-METHYL-3-(3,4-METHYLENEDIOXY-PHENYL) PROPANAL AND PROCESS FOR PRODUCING THE SAME

(75) Inventors: Takashi Doi, Yamaguchi (JP); Yoshihiro Yoshida, Yamaguchi (JP); Eiji Sajiki, Chiba (JP); Satoru Fujitsu, Yamaguchi (JP)

(73) Assignee: Ube Industries, Ltd., Ube-shi (JP)

( * ) Notice: Subject to any disclaimer, the term of this patent is extended or adjusted under 35 U.S.C. 154(b) by 0 days.

(21) Appl. No.: 13/214,408

(22) Filed: Aug. 22, 2011

(65) Prior Publication Data

US 2011/0301361 A1  Dec. 8, 2011

Related U.S. Application Data

(62) Division of application No. 12/529,719, filed as application No. PCT/JP2008/054053 on Mar. 6, 2008, now Pat. No. 8,039,649.

(30) Foreign Application Priority Data

Mar. 7, 2007  (JP) ................................ 2007-056686

(51) Int. Cl.
  *C07D 317/44* (2006.01)
(52) U.S. Cl. ....................................................... 549/446
(58) Field of Classification Search .................... 549/446
  See application file for complete search history.

(56) References Cited

U.S. PATENT DOCUMENTS

| 3,008,968 | A | 11/1961 | Muus et al. |
| 8,039,649 | B2 * | 10/2011 | Doi et al. ..................... 549/446 |
| 2006/0004213 | A1 | 1/2006 | Shirai et al. |
| 2006/0069273 | A1 | 3/2006 | Shirai et al. |
| 2010/0121085 | A1 | 5/2010 | Doi et al. |

FOREIGN PATENT DOCUMENTS

| JP | 55 141437 | 11/1980 |
| JP | 57 45124 | 3/1982 |
| JP | 10-120674 | 5/1998 |
| JP | 2005 239619 | 9/2005 |
| JP | 2006 104151 | 4/2006 |
| JP | 2007 126436 | 5/2007 |
| WO | 2004 054997 | 7/2004 |
| WO | 2006 120639 | 11/2006 |

OTHER PUBLICATIONS

Ohta, Setsuko et al., "Protective Effects of Sesamol and Its Related Compounds on Carbon Tetrachloride Induced Liver Injury in Rats", Journal of the Pharmaceutical Society of Japan, vol. 114, No. 11, p. 803-910, Nov. 1994, (with English abstract).
Uchida, Mihoko et al., "Antioxidative Effect of Sesamol and Related Compounds on Lipid Peroxidation", Biological & Pharmaceutical Bulletin, vol. 19, No. 4, p. 623-626, Apr. 1996.
Extended European Search Report issued on Apr. 26, 2011 in the Application No. 08721473.0.

* cited by examiner

*Primary Examiner* — Nizal Chandrakumar
(74) *Attorney, Agent, or Firm* — Oblon, Spivak, McClelland, Maier & Neustadt, L.L.P.

(57) ABSTRACT

The present invention relates to [1] a method for keeping a quality of 2-methyl-3-(3,4-methylenedioxyphenyl)propanal useful as a perfume, which comprises incorporating from 50 to 3000 ppm of 1-acetyl-3,4-methylenedioxybenzene in the 2-methyl-3-(3,4-methylenedioxyphenyl)propanal; [2] a process for producing 2-methyl-3-(3,4-methylenedioxyphenyl) propanal having a content range from 50 to 3000 ppm of 1-acetyl-3,4-methylenedioxybenzene; and [3] 2-methyl-3-(3,4-methylenedioxyphenyl)propanal having a content range from 50 to 3000 ppm of 1-acetyl-3,4-methylenedioxybenzene.

2 Claims, No Drawings

— 1 —
METHOD OF RETAINING THE QUALITY OF 2-METHYL-3-(3,4-METHYLENEDIOXYPHENYL) PROPANAL AND PROCESS FOR PRODUCING THE SAME

TECHNICAL FIELD

The present invention relates to a method for keeping a quality of 2-methyl-3-(3,4-methylenedioxyphenyl)propanal useful as a perfume, and a process for producing the same.

BACKGROUND ART

It is known that perfume compositions such as fragrance compounds and fragrances are adversely influenced by light, heat, air, etc., in respective stages such as production, distribution and storage and, therefore, suffer from various problems such as deterioration in quality of fragrance with the lapse of time and dissipation of fragrance itself. It is very important to solve these problems for well controlling a quality of fragrance of the perfume compositions. Owing to this reason, many studies have been carried out development of perfume compositions having a less change in fragrance quality with the lapse of time.

In order to solve these problems, it has been generally attempted to add or mix a stabilizer such as, for example, vitamin E, dibutyl hydroxyanisole (BHA) and dibutyl hydroxytoluene (BHT) in perfume-containing products. However, these stabilizers are likely to lose a stabilizing effect by reaction with the perfume itself or induce a change in fragrance of the perfume depending on a mixing amount thereof, or tend to fail to keep their stabilizing effect for a long period of time. Thus, it has been very difficult to suitably select kinds of stabilizers to be mixed and well control their mixing amounts, and there are therefore present only a very small number of stabilizers which are capable of exhibiting sufficient effects for keeping a quality of a perfume which are required for perfume-containing products.

2-Methyl-3-(3,4-methylenedioxyphenyl)propanal is a marine-based perfume extensively used in general perfumes and cosmetics such as, for example, perfumed waters, soaps, shampoos, rinses, detergents, cosmetics, sprays and aromatizing agents (for example, refer to Non-Patent Document 1).

As the method for producing the above compound, there are known the method in which the compound is produced from safrole obtained by purification of sassafras oil via heliotropin and then 2-methyl-3-(3,4-methylenedioxyphenyl)-2-propenal by finally subjecting 2-methyl-3-(3,4-methylenedioxyphenyl)-2-propenal to hydrogenation reaction (for example, refer to Patent Document 1), the method in which the compound is produced via 1-acetoxy-2-methyl-3-(3,4-methylenedioxyphenyl)-1-propene (for example, refer to Patent Documents 2 and 3), etc. In addition, Patent Documents 4 to 7 disclose the method for producing 2-methyl-3-(3,4-methylenedioxyphenyl)propanal from 1,2-methylenedioxybenzene as a starting material. However, these prior documents have failed to specify the method of keeping a quality of the compound.

Also, 2-methyl-3-(3,4-methylenedioxyphenyl)propanal produced by these conventional methods tends to suffer from yellow discoloration in air and, therefore, have such a problem that a perfume prepared from the compound is undesirably colored during production thereof. Further, if the compound used, for example, in living goods or products, is decomposed and deteriorated in quality such as purity and fragrance, the consumers might suffer from problems such as uncomfortable feeling.

— 2 —
Therefore, there is a demand for stabilizers capable of suppressing deterioration in quality of the compound as well as a method for suppressing undesirable coloration and decomposition thereof.

Non-Patent Document 1: Angew. Chem. Int. Ed., 2000, Vol. 39(17), p. 2980
  Patent Document 1: U.S. Pat. No. 3,008,968
  Patent Document 2: JP 57-45124A
  Patent Document 3: JP 2006-104151A
  Patent Document 4: JP 55-141437A
  Patent Document 5: JP 2005-239619A
  Patent Document 6: WO 2004/054997
  Patent Document 7: WO 2006/120639

DISCLOSURE OF THE INVENTION

Problem to be Solved by the Invention

An object of the present invention is to provide a method for keeping a quality of 2-methyl-3-(3,4-methylenedioxyphenyl)propanal useful as a perfume, and a process for producing the same.

Means for Solving the Problem

As the result of intensive studies on undesirable coloration and decomposition of 2-methyl-3-(3,4-methylenedioxyphenyl)propanal as a raw perfume material which have been encountered upon production and storage of the compound, the present inventors have found that 1-acetyl-3,4-methylenedioxybenzene is effective to suppress the coloration and decomposition. In addition, as a result of intensive studies on a requiring amount of 1-acetyl-3,4-methylenedioxybenzene which is however free from occurrence of deterioration in fragrance of the raw perfume material, the present inventors have also established an industrially advantageous process for producing 2-methyl-3-(3,4-methylenedioxyphenyl)propanal which is capable of well controlling a requiring amount of 1-acetyl-3,4-methylenedioxybenzene used therein. The present invention has been accomplished on the basis of the above findings.

Thus, the present invention relates to the following aspects [1] to [5].

[1] A method for keeping a quality of 2-methyl-3-(3,4-methylenedioxyphenyl)propanal, comprising:
  incorporating from 50 to 3000 ppm of 1-acetyl-3,4-methylenedioxybenzene in the 2-methyl-3-(3,4-methylenedioxyphenyl)propanal.

[2] A process for producing 2-methyl-3-(3,4-methylenedioxyphenyl)propanal, comprising the steps of:
  (1) reacting 1,2-methylenedioxybenzene and 2-methyl-3,3-diacetoxypropene with each other to produce 1-acetoxy-2-methyl-3-(3,4-methylenedioxyphenyl)-1-propene; and
  (2) subjecting the obtained 1-acetoxy-2-methyl-3-(3,4-methylenedioxyphenyl)-1-propene to hydrolysis reaction or to transesterification reaction with an alcohol, followed by subjecting the resulting reaction mixture to distillative purification, to thereby adjust a content of 1-acetyl-3,4-methylenedioxybenzene as a by-product in the 2-methyl-3-(3,4-methylenedioxyphenyl)propanal to from 50 to 3000 ppm.

[3] A process for producing 2-methyl-3-(3,4-methylenedioxyphenyl)propanal, comprising the steps of:
  (3) reacting 1,2-methylenedioxybenzene, methacrolein and acetic anhydride with each other to produce 1-acetoxy-2-methyl-3-(3,4-methylenedioxyphenyl)-1-propene; and
  (2) subjecting the obtained 1-acetoxy-2-methyl-3-(3,4-methylenedioxyphenyl)-1-propene to hydrolysis reaction or to transesterification reaction with an alcohol, followed by subjecting the resulting reaction mixture to distillative purification, to thereby adjust a content of 1-acetyl-3,4-methylenedioxybenzene as a by-product in the 2-methyl-3-(3,4-methylenedioxyphenyl)propanal to from 50 to 3000 ppm.

[4] A process for producing 2-methyl-3-(3,4-methylenedioxyphenyl)propanal having a content of 1-acetyl-3,4-methylenedioxybenzene of from 50 to 3000 ppm, comprising the step of adding 1-acetyl-3,4-methylenedioxybenzene to 2-methyl-3-(3,4-methylenedioxyphenyl)propanal having a content of 1-acetyl-3,4-methylenedioxybenzene of less than 50 ppm.

[5] 2-Methyl-3-(3,4-methylenedioxyphenyl)propanal having a content of 1-acetyl-3,4-methylenedioxybenzene of from 50 to 3000 ppm.

EFFECT OF THE INVENTION

In accordance with the present invention, there can be provided a method for keeping a quality of 2-methyl-3-(3,4-methylenedioxyphenyl)propanal useful as a perfume, and a process for producing the 2-methyl-3-(3,4-methylenedioxyphenyl)propanal in an industrially advantageous manner. The 2-methyl-3-(3,4-methylenedioxyphenyl)propanal of the present invention is effectively prevented from suffering from undesirable coloration and decomposition and, therefore, useful as a component for perfumes and cosmetics.

BEST MODE FOR CARRYING OUT THE INVENTION

[Quality Keeping Method]

The method for keeping a quality of 2-methyl-3-(3,4-methylenedioxyphenyl)propanal according to the present invention is characterized by incorporating from 50 to 3000 ppm of 1-acetyl-3,4-methylenedioxybenzene in the 2-methyl-3-(3,4-methylenedioxyphenyl)propanal.

The content of 1-acetyl-3,4-methylenedioxybenzene in 2-methyl-3-(3,4-methylenedioxyphenyl)propanal is from 50 to 3000 ppm, preferably from 55 to 2900 ppm, more preferably from 60 to 2800 ppm, still more preferably from 65 to 2500 ppm, further still more preferably from 65 to 1200 ppm and most preferably from 65 to 500 ppm from the viewpoints of effectively preventing occurrence of undesirable coloration and decomposition of 2-methyl-3-(3,4-methylenedioxyphenyl)propanal and suppressing adverse influence on fragrance thereof.

2-methyl-3-(3,4-methylenedioxyphenyl)propanal containing within the range from 50 to 3000 ppm of 1-acetyl-3,4-methylenedioxybenzene exhibits a good safety as a product similar to that of commercially available products for the Ames test as well as tests for acute toxicity, primary skin irritation, ocular mucous membrane irritation, and so on. Therefore, it can be used without any significant problems.

The 2-methyl-3-(3,4-methylenedioxyphenyl)propanal containing from 50 to 3000 ppm of 1-acetyl-3,4-methylenedioxybenzene which is capable of keeping a good quality thereof may be produced in an industrially advantageous manner by the following three processes (A) to (C).

(1) Production Process (A):

The production process (A) comprises the steps of (1) reacting 1,2-methylenedioxybenzene and 2-methyl-3,3-diacetoxypropene with each other to produce 1-acetoxy-2-methyl-3-(3,4-methylenedioxyphenyl)-1-propene; and (2) subjecting the obtained 1-acetoxy-2-methyl-3-(3,4-methylenedioxyphenyl)-1-propene to hydrolysis reaction or to transesterification reaction with an alcohol, followed by subjecting the resulting reaction mixture to distillative purification, to thereby adjust a content of 1-acetyl-3,4-methylenedioxybenzene as a by-product in the 2-methyl-3-(3,4-methylenedioxyphenyl)propanal to from 50 to 3000 ppm.

Production Process (B):

The production process (B) comprises the steps of (3) reacting 1,2-methylenedioxybenzene, methacrolein and acetic anhydride with each other to produce 1-acetoxy-2-methyl-3-(3,4-methylenedioxyphenyl)-1-propene; and (2) subjecting the obtained 1-acetoxy-2-methyl-3-(3,4-methylenedioxyphenyl)-1-propene to hydrolysis reaction or to transesterification reaction with an alcohol, followed by subjecting the resulting reaction mixture to distillative purification, to thereby adjust a content of 1-acetyl-3,4-methylenedioxybenzene as a by-product in the 2-methyl-3-(3,4-methylenedioxyphenyl)propanal to from 50 to 3000 ppm.

(3) Production Process (C):

The production process (C) comprises the step of adding 1-acetyl-3,4-methylenedioxybenzene to 2-methyl-3-(3,4-methylenedioxyphenyl)propanal having a content of 1-acetyl-3,4-methylenedioxybenzene of less than 50 ppm to thereby adjust the content of 1-acetyl-3,4-methylenedioxybenzene therein to a suitable level.

The production processes (A) and (B) relate to a method utilizing 1-acetyl-3,4-methylenedioxybenzene by-produced in the course of production of 2-methyl-3-(3,4-methylenedioxyphenyl)propanal in which an amount of 1-acetyl-3,4-methylenedioxybenzene to be incorporated in 2-methyl-3-(3,4-methylenedioxyphenyl)propanal is controlled to a desired level. Whereas, the production process (C) relates to a method in which 1-acetyl-3,4-methylenedioxybenzene is subsequently added to the produced 2-methyl-3-(3,4-methylenedioxyphenyl)propanal to suitably control the content of 1-acetyl-3,4-methylenedioxybenzene therein.

In the followings, the production processes (A) to (C) are respectively explained in more detail.

[Production Process (A)]

The production process (A) comprises the step (1) of reacting 1,2-methylenedioxybenzene represented by the following formula (1) and 2-methyl-3,3-diacetoxypropene represented by the following formula (2) with each other to produce 1-acetoxy-2-methyl-3-(3,4-methylenedioxyphenyl)-1-propene represented by the following formula (3); and the step (2) of subjecting the obtained 1-acetoxy-2-methyl-3-(3,4-methylenedioxyphenyl)-1-propene to hydrolysis reaction or to transesterification reaction with an alcohol, followed by subjecting the resulting reaction mixture to distillative purification.

Step (1)

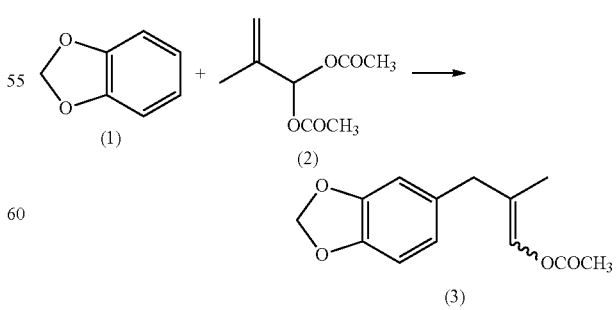

Meanwhile, in the formula (3), the acetoxy group is illustrated as being bonded to a cis- or trans-position.

(Production of 2-Methyl-3,3-Diacetoxypropene [Formula (2)])

The process for production of 2-methyl-3,3-diacetoxypropene used as a raw material in the production process (A) is not particularly limited. For example, 2-methyl-3,3-diacetoxypropene may be produced by a process in which methacrolein is reacted with acetic anhydride in the presence of a catalyst (refer to JP 61-151152A), etc.

Examples of the reaction method used in these production processes include a continuous method, a semi-continuous method and a batch method. Any of these reaction methods may be used without particular limitations.

In the process in which methacrolein and acetic anhydride are reacted with each other, compounds having a Lewis acid property or Brønsted acids may be used as the catalyst.

Examples of the compounds having a Lewis acid property include boron halides compounds (boron trifluoride, boron trichloride, boron tribromide, boron triiodide, a boron trifluoride-acetic acid complex, a boron trifluoride-diacetic acid complex, a boron trifluoride-diethyl ether complex, a boron trifluoride-tetrahydrofuran complex, a boron trifluoride-acetonitrile complex, boron trifluoride dihydrate, a boron trifluoride-n-butyl ether complex, a boron trifluoride-dimethyl ether complex, a boron trifluoride-methanol complex, a boron trifluoride-phenol complex and a boron trifluoride-phosphoric acid complex, etc.); metal halides (aluminum fluoride, aluminum chloride, aluminum bromide, aluminum iodide, gallium fluoride, gallium chloride, gallium bromide, gallium iodide, indium fluoride, indium chloride, indium bromide, indium iodide, scandium chloride, scandium bromide, scandium iodide, yttrium chloride, yttrium bromide, yttrium iodide, titanium tetrachloride, titanium tetrabromide, titanium tetraiodide, zirconium tetrachloride, zirconium tetrabromide, zirconium tetraiodide, hafnium tetrachloride, hafnium tetrabromide, hafnium tetraiodide, iron trifluoride, iron trichloride, iron dichloride, iron tribromide, iron triiodide, ruthenium trifluoride, ruthenium trichloride, ruthenium tribromide, ruthenium triiodide, zinc fluoride, zinc chloride, zinc bromide, zinc iodide, cadmium fluoride, cadmium chloride, cadmium bromide, cadmium iodide, mercury fluoride, mercury chloride, mercury bromide, tin fluoride, tin chloride, tin bromide, tin iodide, antimony fluoride, antimony chloride, antimony bromide, antimony iodide and trihalides of lanthanoids having an atomic number of from 57 to 71, etc.); metal triflate compounds (copper triflate, copper trifluoroacetate, silver triflate, silver trifluoroacetate, zinc triflate, zinc trifluoroacetate, cadmium triflate, tin triflate, scandium triflate, yttrium triflate and triflates of lanthanoids having an atomic number of from 57 to 71, etc.); and metal trifluoroacetate compounds (such as cadmium trifluoroacetate, tin trifluoroacetate, scandium trifluoroacetate, yttrium trifluoroacetate and trifluoroacetates, etc.).

Examples of the Brønsted acids include hydrogen fluoride, hydrochloric acid, hydrogen bromide, hydrogen iodide, trifluoroacetic acid, acetic acid, oxalic acid, phosphoric acid, sulfuric acid, methanesulfonic acid and toluenesulfonic acid.

Meanwhile, the above compounds having a Lewis acid property and the Brønsted acids may be respectively used alone or in combination of any two or more thereof.

The amount of the catalyst used is not particularly limited. The catalyst is usually used in a catalytic amount, e.g., in an equimolar amount or less, based on methacrolein. However, in case where the reaction proceeds too slowly or no reaction proceeds, the catalyst may be used in an equimolar amount or more based on methacrolein.

No solvent is usually used in the reaction. However, the solvent may be used, if desired. Examples of the solvent include hydrocarbon compounds (hexane, heptane, benzene and toluene, etc.); carboxylic acids (acetic acid and propionic acid, etc.); carboxylic acid esters (methyl acetate, ethyl acetate and ethyl propionate, etc.); ethers (diethyl ether and diisopropyl ether, etc.); and aprotic polar solvents (acetonitrile and N,N-dimethyl imidazolidinone, etc.).

The feeding molar ratio between methacrolein and acetic anhydride is not particularly limited. The molar ratio of acetic anhydride to methacrolein (acetic anhydride/methacrolein) is usually from 0.5 to 2.5 and preferably from 1.0 to 1.5.

The reaction temperature is also not particularly limited. However, the reaction temperature is usually from −30 to 65° C. and preferably from 0 to 40° C.

The thus produced 2-methyl-3,3-diacetoxypropene may be subjected, after completion of the reaction, to purification treatments such as water-washing, neutralization and distillation, and then used as a raw material in the step (1). Alternatively, the 2-methyl-3,3-diacetoxypropene may be used as such without being subjected to any purification treatments.

(Production of 1-acetoxy-2-methyl-3-(3,4-methylenedioxyphenyl)-1-propene [Formula (2)])

In the production process (A), the method for production of 1-acetoxy-2-methyl-3-(3,4-methylenedioxyphenyl)-1-propene is not particularly limited. For example, 1-acetoxy-2-methyl-3-(3,4-methylenedioxyphenyl)-1-propene may be produced by the methods described in Patent Documents 2, 4, 6 and 7.

The reactions in these methods may be carried out by any of a continuous method, a semi-continuous method and a batch method, etc.

In the above reaction system, the feeding molar ratio of 1,2-methylenedioxybenzene [formula (1)] to 2-methyl-3,3-diacetoxypropene [formula (2)] (1,2-methylenedioxybenzene/2-methyl-3,3-diacetoxypropene) is not particularly limited, and is usually from 0.5 to 50, preferably from 2 to 10 and more preferably from 3 to 6.

In case of reacting 2-methyl-3,3-diacetoxypropene [formula (2)] with 1,2-methylenedioxybenzene [formula (1)], the catalyst, such as the compound having a Lewis acid property and the Brønsted acid as described above, may be used in the reaction. The amount of the catalyst is not particularly limited. The catalyst may be usually used in an amount of not less than 0.001 mol and less than 1 mol, preferably from 0.003 to 0.85 mol, more preferably from 0.004 to 0.50 mol and still more preferably from 0.005 to 0.40 mol, on the basis of 1 mol of 2-methyl-3,3-diacetoxypropene. However, in case where the reaction proceeds too slowly or no reaction proceeds, the catalyst may be used in an equimolar amount or more based on 2-methyl-3,3-diacetoxypropene.

The temperature used upon the reaction between 2-methyl-3,3-diacetoxypropene and 1,2-methylenedioxybenzene is usually from −10 to 80° C. and preferably from 10 to 60° C. When the reaction temperature exceeds 80° C., decomposition of 1-acetoxy-2-methyl-3-(3,4-methylenedioxyphenyl)-1-propene as the reaction product tends to be initiated, whereas when the reaction temperature is lower than −10° C., the reaction tends to proceed too slowly, resulting in poor productivity.

After completion of the reaction, the resulting reaction mixture may be purified by conventional methods such as, for example, extraction, filtration, concentration, distillation, recrystallization, crystallization and column chromatography. From the viewpoint of advantageous industrial processes, among these purification methods, preferred are distillation and crystallization. More specifically, for example in the distillative purification method, after completion of the reaction, the resulting reaction mixture is washed with water, and then the obtained organic layer solution is distilled to remove unreacted 1,2-methylenedioxybenzene, so that a crude product containing 1-acetoxy-2-methyl-3-(3,4-methylenedioxyphenyl)-1-propene [formula (3)] and 1-acetyl-3,4-methylenedioxybenzene represented by the following formula (4) can be obtained in the form of a residue solution. However, it is preferred that the residue solution be further subjected to distillative purification to obtain the crude product containing 1-acetoxy-2-methyl-3-(3,4-methylenedioxyphenyl)-1-propene [formula (3)] and 1-acetyl-3,4-methylenedioxybenzene represented by the following formula (4) as a distillate.

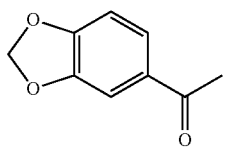

(4)

The removal of the unreacted 1,2-methylenedioxybenzene by distillation is usually carried out at a temperature range from 40 to 175° C. (under a pressure range from 1 to 760 torr) and preferably at a temperature range from 50 to 150° C. (under a pressure of from 3 to 300 torr) in view of a boiling point of 1,2-methylenedioxybenzene (109° C./80 torr) and a boiling point of 1-acetoxy-2-methyl-3-(3,4-methylenedioxyphenyl)-1-propene as the target product (170° C./5 torr). The unreacted 1,2-methylenedioxybenzene thus recovered by distillation may be reused in the step (1).

Meanwhile, the content of 1-acetyl-3,4-methylenedioxybenzene in the obtained crude product varies depending upon a feeding ratio between amounts of acetic anhydride and 1,2-methylenedioxybenzene charged upon the reaction, reaction temperature, kind of catalyst used, etc., and is about 60000 ppm at maximum. It is also suggested that the acetyl group contained in 1-acetyl-3,4-methylenedioxybenzene represented by the following formula (4) is generated from 2-methyl-3,3-diacetoxypropene and acetic anhydride used in the reaction and introduced thereinto by Friedel-Craft reaction.

Alternatively, after completion of the reaction, the resulting reaction mixture may be subjected to post-treatments only for the purpose of decomposing and washing out the catalyst used, without any of the above procedures including removal of the unreacted 1,2-methylenedioxybenzene by distillation and acquisition of the purified 1-acetoxy-2-methyl-3-(3,4-methylenedioxyphenyl)-1-propene by distillation, or may be used as a material in the next step (2) merely after decomposing the catalyst, etc., by adding an acid, a based or a salt thereto in stead of washing with water, etc.

Step (2)

In the step (2), 1-acetoxy-2-methyl-3-(3,4-methylenedioxyphenyl)-1-propene represented by the following formula (3) which has been obtained in the step (1) is subjected to hydrolysis reaction or to transesterification reaction with an alcohol to obtain a crude product of 1-acetyl-3,4-methylenedioxybenzene represented by the following formula (4) and 2-methyl-3-(3,4-methylenedioxyphenyl)propanal represented by the following formula (5), and then the resulting reaction mixture is further subjected to distillative purification, to thereby obtain 2-methyl-3-(3,4-methylenedioxyphenyl)propanal having a content of 1-acetyl-3,4-methylenedioxybenzene of from 50 to 3000 ppm.

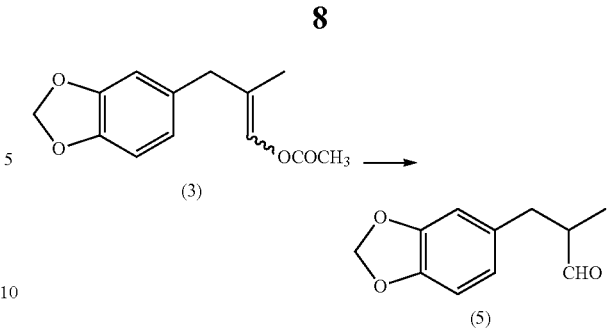

Meanwhile, in the formula (3), the acetoxy group is illustrated as being bonded to a cis- or trans-position.

(Hydrolysis Reaction)

The hydrolysis reaction may be carried out by any of a batch method, a semi-continuous method and a continuous method. The hydrolysis reaction may be carried out in the presence of water. Also, an organic solvent may be used in the hydrolysis reaction in order to improve the mixing water with 1-acetoxy-2-methyl-3-(3,4-methylenedioxyphenyl)-1-propene. The amount and kind of the organic solvent used in the hydrolysis reaction is not particularly limited unless the addition thereof has an adverse influence on the reaction. Examples of the organic solvent include alcohols (methyl alcohol, ethyl alcohol, isopropyl alcohol, n-propyl alcohol, n-butyl alcohol, isobutyl alcohol, sec-butyl alcohol, tert-butyl alcohol, ethylene glycol and propylene glycol, etc.); aliphatic carboxylic acids (acetic acid, propionic acid and butyric acid, etc.); aliphatic carboxylic acid esters (methyl acetate, ethyl acetate, methyl propionate and ethyl propionate, etc.); and aprotic polar solvents (acetonitrile, tetrahydrofuran, N,N-dimethylformamide, N,N-dimethyl imidazolidinone, N-methylpyrrolidone, dimethyl sulfoxide and hexamethyl phosphoric triamide, etc.). These organic solvents may be used alone or in combination of any two or more thereof. In addition, these organic solvent may be recovered after the reaction, and reused.

The catalyst used in the hydrolysis reaction may be either an acid catalyst or a base catalyst.

Examples of the acid catalyst include hydrogen fluoride, hydrogen chloride, hydrogen bromide, hydrogen iodide, oxalic acid, sulfuric acid, hydrochloric acid, phosphoric acid, sodium dihydrogenphosphate, sodium monohydrogenphosphate, nitric acid, formic acid, acetic acid, propionic acid, acid ion exchange resins and zeolites having an acidic point.

Examples of the base catalyst include hydroxides of alkali metals or alkali earth metals (lithium hydroxide, sodium hydroxide, potassium hydroxide, rubidium hydroxide, cesium hydroxide, magnesium hydroxide, calcium hydroxide and strontium hydroxide, etc.); carbonates of alkali metals or alkali earth metals (lithium carbonate, sodium carbonate, potassium carbonate, rubidium carbonate, cesium carbonate, magnesium carbonate, calcium carbonate and strontium carbonate, etc.); alkoxides of alkali metals or alkali earth metals (lithium methoxide, sodium methoxide, potassium methoxide, rubidium methoxide, cesium methoxide, calcium methoxide and magnesium methoxide, etc.); carboxylates of alkali metals or alkali earth metals (sodium acetate, potassium acetate, sodium oxalate and potassium oxalate, etc.); phosphates of alkali metals or alkali earth metals (sodium phosphate, etc.); basic ion exchange resins; and zeolites having a basic point.

These acid catalysts and base catalysts may be respectively used alone or in combination of any two or more thereof.

The amount of the catalyst used varies depending upon kind thereof, and is usually 1 mol or less, preferably from 0.001 to 0.5 mol and more preferably from 0.005 to 0.3 mol on the basis of 1 mol of 1-acetoxy-2-methyl-3-(3,4-methylenedioxyphenyl)-1-propene. However, in case where the reaction proceeds too slowly or no reaction proceeds, the catalyst may be used in an equimolar amount or more based on 1-acetoxy-2-methyl-3-(3,4-methylenedioxyphenyl)-1-propene.

In the hydrolysis reaction, the amount of water usually from 1 to 50 mol, preferably from 1.5 to 30 mol and more preferably from 3 to 20 mol on the basis of 1 mol of 1-acetoxy-2-methyl-3-(3,4-methylenedioxyphenyl)-1-propene.

The temperature on the hydrolysis reaction varies depending upon kind and amount of the catalyst used and kind of the solvent used, and is preferably from 20 to 120° C. and more preferably from 30 to 100° C.

(Transesterification Reaction with Alcohol)

In the step (2), 1-acetoxy-2-methyl-3-(3,4-methylenedioxyphenyl)-1-propene [formula (3)] obtained in the step (1) may also be subjected to transesterification reaction with an alcohol. In the transesterification reaction, an acetic acid ester of the alcohol used is by-produced.

The transesterification reaction may be carried out by any of a continuous method, a semi-continuous method and a batch method.

Examples of the alcohol used in the transesterification reaction include monohydric alcohols such as methanol, ethanol, isopropyl alcohol, n-propyl alcohol, n-butanol, isobutanol, sec-butyl alcohol, tert-butyl alcohol and n-octanol; and polyhydric alcohols such as ethylene glycol, propylene glycol, 1,4-butanediol and glycerol. These alcohols may be used alone or in combination of any two or more thereof.

The amount of the alcohol used in the transesterification reaction is not particularly limited, and is usually from 1 to 50 mol, preferably from 1.2 to 30 mol and more preferably from 1.5 to 20 mol on the basis of 1 mol of 1-acetoxy-2-methyl-3-(3,4-methylenedioxyphenyl)-1-propene. The unreacted alcohol may be recovered and reused in the transesterification reaction.

The catalyst used in the transesterification reaction is not particularly limited, and may be any known suitable catalyst such as an acid catalyst, a base catalyst and a metal catalyst. Examples of the acid catalyst and the base catalyst include the same catalysts as described above in the hydrolysis reaction.

The metal catalyst is not particularly limited. Examples of the metal catalyst include titanium compounds, such as titanium alkoxides (titanium tetramethoxide, titanium tetraethoxide, titanium tetraisopropoxide and titanium tetrabutoxide, etc.); tin compounds (dibutyl tin oxide, dibutyl tin diacetate, dibutyl tin dilaurate and tin oxide, etc.); and lead compounds (lead acetate and lead oxide, etc.). These metal catalysts may be used alone or in combination of any two or more thereof.

The amount of the catalyst used in the transesterification reaction varies depending upon kind thereof, and is usually 1 mol or less, preferably from 0.001 to 0.5 mol and more preferably from 0.005 to 0.3 mol on the basis of 1 mol of 1-acetoxy-2-methyl-3-(3,4-methylenedioxyphenyl)-1-propene.

Also, in order to enhance a solubility of the catalyst used, an organic solvent may be optionally added to the reaction system. The organic solvent used for the above purpose may be appropriately determined according to the kind of catalyst used, and not particularly limited as long as the solvent added serves for enhancing a solubility of the catalyst therein and is inert to the reaction. Examples of the organic solvent include aliphatic carboxylic acids (acetic acid, propionic acid and butyric acid, etc.); aliphatic carboxylic acid esters (methyl acetate, ethyl acetate, methyl propionate and ethyl propionate, etc.); halogen compounds (methylene chloride, chloroform and chlorobenzene, etc.); and aprotic polar solvents (acetonitrile, tetrahydrofuran, N,N-dimethylformamide, N,N-dimethyl imidazolidinone, N-methylpyrrolidone, dimethyl sulfoxide and hexamethyl phosphoric triamide, etc.). These organic solvents may be used alone or in combination of any two or more thereof. In addition, these organic solvent may be recovered after the reaction, and reused.

The temperature of the transesterification reaction varies depending upon kind of alcohol used and amount of catalyst used, and is usually from 0 to 150° C., preferably from 20 to 120° C. and more preferably from 30 to 100° C.

In the reaction of the step (2), in case where the amount of residual 1-acetoxy-2-methyl-3-(3,4-methylenedioxyphenyl)-1-propene [formula (3)] is too large, the compound [formula (3)] tends to be gradually decomposed in the subsequent distillative purification step, resulting in generation of acetic acid. Therefore, the conversion yield of 1-acetoxy-2-methyl-3-(3,4-methylenedioxyphenyl)-1-propene is preferably 90% or more, more preferably 95% or more, and still more preferably 98% or more.

The reaction mixture obtained after the hydrolysis reaction or the transesterification reaction in the step (2) contains the catalyst used therein. Therefore, the reaction mixture may be subjected to post-treatments such as neutralization of the catalyst with an acid or a base, and washing treatment with water, an acidic aqueous solution or a basic aqueous solution for removal of the catalyst, thereby obtaining a crude product containing 1-acetyl-3,4-methylenedioxybenzene [formula (4)] and 2-methyl-3-(3,4-methylenedioxyphenyl)propanal [formula (5)]. In addition, the thus obtained crude product may be further subjected to distillation for the purpose of removing the reaction residue therefrom to obtain a fresh crude product containing 2-methyl-3-(3,4-methylenedioxyphenyl)propanal [formula (5)] and 1-acetyl-3,4-methylenedioxybenzene [formula (4)] as a distillate.

On the other hand, the reaction mixture may also be subjected to distillation for removal of water, alcohols, organic solvents which used in the reaction, etc., therefrom without conducting the neutralization or washing, or the reaction mixture obtained after completion of the reaction may be subjected to distillative purification for distilling 2-methyl-3-(3,4-methylenedioxyphenyl)propanal therefrom, thereby obtaining a crude product of 2-methyl-3-(3,4-methylenedioxyphenyl)propanal. However, these methods might be industrially disadvantageous because 2-methyl-3-(3,4-methylenedioxyphenyl)propanal as the target product tends to be decomposed owing to adverse influence of the catalyst residue therein, and tends to occur the further deterioration in quality of the obtained distillate owing to inclusion of the decomposed product therein, etc.

Moreover, in the hydrolysis reaction, acetic acid tends to be by-produced. Therefore, the reaction mixture may be subjected to washing post-treatment with water or a basic solution to effectively remove the acetic acid from the resulting 2-methyl-3-(3,4-methylenedioxyphenyl)propanal.

(Distillative Purification)

Next, the distillative purification of the crude product containing 1-acetyl-3,4-methylenedioxybenzene [formula (4)] and 2-methyl-3-(3,4-methylenedioxyphenyl)propanal [formula (5)] is explained.

The distillative purification may be carried out by either a simple distillation method or a rectification method. The respective distillation methods may be carried out by any of a batch method, a semi-continuous method and a continuous method.

Since it is necessary to conduct the distillation while finely controlling the amount of 1-acetyl-3,4-methylenedioxybenzene [formula (4)] included in the main fraction, a rectifier is preferably attached to a distillation apparatus. Meanwhile, the number of rectifiers and frequency of distillation procedures are not particularly limited.

As the rectifier, there may be used those ordinarily used for distillative purification such as a plate column-type rectifier and a packed column-type rectifier.

The packing material used in the packed column-type rectifier is not particularly limited. However, since 2-methyl-3-(3,4-methylenedioxyphenyl)propanal tends to be decomposed with increasing the distillation temperature, a regular packing material is preferably used so as to exclude a need of setting a liquid temperature in a distillation still to a high level and reduce a difference in pressure between a top and bottom of the rectifier.

Examples of the regular packing material used include "SULZER PACKING" (wire mesh-molded type) and "MELLAPAK" (porous metal sheet-molded type) both available from Sulzer Chemtech Ltd., "GEMPAK" available from Glitsch Inc., "MONTZ-PAK" available from Monz GmbH & Co KG, "GOOD ROLL PACKING" available from Nippon Filcon Co., Ltd., "HONEYCOMB PAK" available from NGK Insulators, Ltd., "IMPULSE PACKING" available from Nagaoka Co., Ltd., "MC PAK" (wire mesh-molded type or metal sheet-molded type), and "TECHNOPAK". Examples of materials for the rectifier or the packing material include those materials ordinarily used for distillative purification such as stainless steel, Hastelloy, ceramics, and resins.

The heating method used upon the distillation is not particularly limited, and may be selected from those methods using an conventional heat exchanger of a jacket type, a coil type, a falling film type, a thin film type, etc. In this case, in order to suppress thermal decomposition of 2-methyl-3-(3,4-methylenedioxyphenyl)propanal [formula (5)], it is preferred to use a thin film-type evaporator or a falling film-type evaporator, which has a short residence time upon contact with a heat transfer surface. For example, a heating device such as a falling film-type evaporator may be connected to the rectifier to suppress thermal decomposition of 2-methyl-3-(3,4-methylenedioxyphenyl)propanal [formula (5)] itself in the reaction mixture in case of subjecting the reaction mixture to distillative purification.

The plate (tray) used in the plate column-type rectifier is not particularly limited.

The actual number of stages (plates) of the distillative rectifier is usually from 1 to 200, preferably from 2 to 120 and more preferably from 3 to 70.

Moreover, the reflux ratio may be determined by confirming the condition of separation of the mixture in the each rectifiers. The smaller number of stages of the rectifier tend to cause deterioration in separation efficiency, whereas the excessively large number of stages of the rectifier tend to cause deterioration in distillation efficiency. The reflux ratio upon the distillation (refluxed amount/distilled amount) is usually from 0 to 50, preferably from 0.1 to 30 and more preferably from 1 to 15. The excessively large reflux ratio is undesirable since other reactions such as decomposition of 2-methyl-3-(3,4-methylenedioxyphenyl)propanal [formula (5)] tends to be occurred owing to a long heating time.

The boiling point of 1-acetyl-3,4-methylenedioxybenzene [formula (4)] (boiling point: 158 to 159° C./14 torr) is lower than that of 2-methyl-3-(3,4-methylenedioxyphenyl)propanal [formula (5)] (boiling point: 158° C./10 torr). For this reason, in the distillation of the step (2), it is preferred that the following three fractions (distillates 1, 2 and 3) be obtained.

That is, the distillate 1 is 2-methyl-3-(3,4-methylenedioxyphenyl)propanal containing 1-acetyl-3,4-methylenedioxybenzene [formula (4)] in an amount of more than 3000 ppm; the distillate 2 is 2-methyl-3-(3,4-methylenedioxyphenyl)propanal containing 1-acetyl-3,4-methylenedioxybenzene in an amount of from 50 to 3000 ppm as the target product of the present invention; and the distillate 3 is 2-methyl-3-(3,4-methylenedioxyphenyl)propanal containing 1-acetyl-3,4-methylenedioxybenzene in an amount of less than 50 ppm. These three fractions are preferably obtained by distillation in the above order.

The distillative purification is preferably carried out by controlling a liquid temperature in a distillation still of the distillation apparatus to 210° C. or lower. More specifically, the liquid temperature under reduced pressure (0.1 to 100 torr (0.013 to 13.332 kPa)) at a top of the rectifier is preferably controlled to from 100 to 210° C., more preferably from 140 to 210° C. and still more preferably from 150 to 200° C. In addition, the liquid temperature in a distillation still of the distillation apparatus when obtaining the final product (upon distillation of the main fraction) is 210° C. or lower, preferably from 125 to 210° C., more preferably from 130 to 200° C., still more preferably from 135 to 190° C., further still more preferably from 140 to 185° C. and most preferably from 145 to 180° C. In case where the liquid temperature exceeds 210° C., even though no by-products nor impurities having a high boiling point are present in the solution in the distillation still, 2-methyl-3-(3,4-methylenedioxyphenyl)propanal itself tends to be decomposed under such a high temperature to produce acetic acid, and the thus produced acetic acid tends to be undesirably included in the main fraction.

On the other hand, the distillation at a low liquid temperature in the distillation still requires a high vacuum. For this purpose, it is necessary to use a special vacuum pump having a high performance, resulting in increase in size of the rectifier used which is disadvantageous from the economical viewpoint. Therefore, in order to obtain 2-methyl-3-(3,4-methylenedioxyphenyl)propanal having a content of 1-acetyl-3,4-methylenedioxybenzene of from 50 to 3000 ppm as the final product, the distillative purification is preferably carried out under the above-specified liquid temperature conditions.

In particular, when the distillative purification is carried out by a batch method, the residence time of 2-methyl-3-(3,4-methylenedioxyphenyl)propanal in the rectifier tends to be prolonged as compared to that of a continuous rectification method. As a result, the distillation efficiency tends to be deteriorated owing to thermal decomposition of the compound, and further acetic acid tends to be by-produced and included in the main fraction. For this reason, in the batch method, the distillation is preferably conducted at a temperature of from 130 to 210° C. and more preferably from 140 to 185° C. Meanwhile, feeding of materials to be distilled as well as withdrawal and storage of the respective fractions and the final product are preferably carried out in an inert gas atmosphere. In some cases, an inert gas may be fed into the reaction system even during distillation under reduced pressure.

Meanwhile, in the above distillative purification, it is also possible to obtain 2-methyl-3-(3,4-methylenedioxyphenyl) propanal [formula (5)] having an acetic acid content (less than 40 ppm) which gives no significant influence on fragrance thereof.

Further, the distillate 2 obtained by the above distillative purification (2-methyl-3-(3,4-methylenedioxyphenyl)propanal having a content of 1-acetyl-3,4-methylenedioxybenzene of from 50 to 3000 ppm as the target product of the present invention) may be used as such as the final product. Therefore, in the distillative purification, it is preferred to do suitable procedures such as analysis of contents of 1-acetyl-3,4-methylenedioxybenzene and acetic acid in the distilled fractions, and to obtain the distillate 2 as the final product be initiated, when the purity of 2-methyl-3-(3,4-methylenedioxyphenyl)propanal therein reaches preferably 95% or more and more preferably 97% or more. Meanwhile, among the fractions other than the distillate 2, for example, the distillate 1 recovered (2-methyl-3-(3,4-methylenedioxyphenyl)propanal having a content of 1-acetyl-3,4-methylenedioxybenzene of more than 3000 ppm) may be carried out again to the similar distillative purification, whereas the distillate 3 recovered (2-methyl-3-(3,4-methylenedioxyphenyl)propanal having a content of 1-acetyl-3,4-methylenedioxybenzene of less than 50 ppm) may be used in the production process (C).

[Production Process (B)]

The production process (B) comprises the step (3) of reacting 1,2-methylenedioxybenzene [formula (1)], methacrolein and acetic anhydride with each other to produce 1-acetoxy-2-methyl-3-(3,4-methylenedioxyphenyl)-1-propene [formula (3)]; and the step (2) of subjecting the obtained 1-acetoxy-2-methyl-3-(3,4-methylenedioxyphenyl)-1-propene [formula (3)] to hydrolysis reaction or to transesterification reaction with an alcohol, followed by subjecting the resulting reaction mixture to distillative purification.

Step (3)

The concrete method for carrying out the step (3) is not particularly limited. For example, the synthesis of the step (3) may be carried out by the method described in Patent Document 7.

The molar ratio between methacrolein and acetic anhydride charged is not particularly limited. The molar ratio of acetic anhydride to methacrolein (acetic anhydride/methacrolein) is usually from 0.5 to 2.5 and preferably from 1.0 to 1.5.

Moreover, the molar ratio between methacrolein and 1,2-methylenedioxybenzene charged is not particularly limited. The molar ratio of 1,2-methylenedioxybenzene to methacrolein (1,2-methylenedioxybenzene/methacrolein) is usually from 0.5 to 50, preferably from 2 to 10 and more preferably from 3 to 6.

In the reaction of the step (3), a compound having a Lewis acid property or a Brønsted acid may be used as a catalyst. The amounts of the catalyst used, reaction temperature and post-treatments conducted after completion of the reaction are the same as those conditions for production of 1-acetoxy-2-methyl-3-(3,4-methylenedioxyphenyl)-1-propene as explained in the step (1) of the production process (A).

The step (2) following the step (3) is the same as the step (2) of the production process (A).

[Production Process (C)]

The production process (C) comprises the step of adding 1-acetyl-3,4-methylenedioxybenzene to 2-methyl-3-(3,4-methylenedioxyphenyl)propanal [formula (5)] having a content of 1-acetyl-3,4-methylenedioxybenzene of less than 50 ppm to adjust the content of 1-acetyl-3,4-methylenedioxybenzene in 2-methyl-3-(3,4-methylenedioxyphenyl)propanal to from 50 to 3000 ppm.

Examples of the 2-methyl-3-(3,4-methylenedioxyphenyl) propanal having a content of 1-acetyl-3,4-methylenedioxybenzene of less than 50 ppm include a purified product of 2-methyl-3-(3,4-methylenedioxyphenyl)propanal obtained in the production process (A) or (B), and a purified product of 2-methyl-3-(3,4-methylenedioxyphenyl)propanal produced by using safrole or heliotropin as a raw material as described, for example, in Patent Document 1.

According to the production processes (A) to (C), 2-methyl-3-(3,4-methylenedioxyphenyl)propanal having a content of 1-acetyl-3,4-methylenedioxybenzene of 50 to 3000 ppm can be produced favorably in an industrially manner. From the results of Ames test as well as tests for acute toxicity, primary skin irritation, ocular mucous membrane irritation, etc., it has been confirmed that the safety of the resulting compound as a perfume product is substantially identical to that of commercially available products and, therefore, the compound can be used without any significant problems. In addition, it has also been confirmed that 2-methyl-3-(3,4-methylenedioxyphenyl)propanal produced by these production processes contains acetic acid which is generated by thermal decomposition of the compound and included therein during the production process thereof and gives adverse influence on a fragrance thereof, in an amount of less than 40 ppm. Therefore, 2-methyl-3-(3,4-methylenedioxyphenyl)propanal produced by the above production processes of the present invention can exhibit a fresher and clearer fragrance different from those of the conventional products produced from safrole or heliotropin. Further, in the production processes (A) and (B), it is not required to separately add a stabilizer for suppressing undesirable coloration and decomposition of 2-methyl-3-(3,4-methylenedioxyphenyl)propanal. As a result, these production processes have some excellent efficiencies in manufacturing production.

EXAMPLES

The present invention will be described in more detail below by referring to the following Examples and Comparative Examples. Meanwhile, in the following Examples and Comparative Examples, "%" means "% by weight" unless otherwise specified.

The measuring methods and methods for calculating a purity, etc., are as follows.

[1] Measurement of Purity of 2-Methyl-3-(3,4-Methylenedioxyphenyl)Propanal as Final Product and Content of 1-Acetyl-3,4-Methylenedioxybenzene The purity and content were calculated by an area percentage method from respective values measured using a gas chromatographic apparatus "GC-2014" available from Shimadzu Corporation (detector: FID system; analyzing column: "TC-17" (0.25 mm×30 m; membrane thickness: 0.5 μm) available from GL Sciences Inc.).

The purity of 2-methyl-3-(3,4-methylenedioxyphenyl) propanal was calculated from an area percentage thereof as measured by gas chromatography, and the content of 1-acetyl-3,4-methylenedioxybenzene was calculated by a modified area percentage method using 2-methyl-3-(3,4-methylenedioxyphenyl)propanal as a standard substance (limit of detection: 10 ppm or less).

Analyzing conditions used in gas chromatography (GC) are as follows: split ratio: 30; injection temperature: 280° C.; detector temperature: 300° C.; column temperature: it was raised from 130° C. up to 280° C. at a temperature rise rate of 5° C./min and maintained at 280° C. for 5 min; amount of sample injected: 0.3 μL

[2] Measurement of Content of Acetic Acid

The content of acetic acid was calculated by an absolute calibration curve method from the value measured using a gas chromatographic apparatus "GC-14B" available from Shimadzu Corporation (detector: FID system; analyzing column: "TC-WAX" (0.53 mm×30 m; membrane thickness: 1.0 μm) available from GL Sciences Inc.).

2-Methyl-3-(3,4-methylenedioxyphenyl)propanal as an object of analysis was injected in an amount of 0.6 μL using a 1 μL microsyringe. The injection temperature and detector temperature were adjusted to 220° C. and 260° C., respectively. The column temperature was maintained at 80° C. for 3 min and then raised up to 115° C. at a temperature rise rate of 5° C./min, and further raised up to 230° C. at a temperature rise rate of 40° C./min and maintained at 230° C. of 20 min.

[3] Measurement of Purity of Crude Product of 2-Methyl-3-(3,4-Methylenedioxyphenyl)Propanal Using a high performance liquid chromatography apparatus (HPLC) "CLASS-VP" available from Shimadzu Corporation (analyzing column: "TSKgel ODS-80Ts QA" (4.6 mm×250 mm) available from Tosoh Corp.), and an eluent containing acetonitrile and a 0.1% phosphoric acid aqueous solution at a volume ratio of 40/60. A pH value and a flow rate of a sample were adjusted to 2.5 and 1.0 mL/min, respectively, and a column oven temperature was set to 40° C. Using a UV detector, the purity of the sample was measured by using a measuring wavelength of 252 nm and controlling an amount of the sample injected to 20 μL, and calculated from the thus measured value by an area percentage method.

The sample was prepared as follows. That is, 0.8 g of a sample liquid to be measured was accurately weighed and placed in a 50 mL measuring flask, and then diluted with acetonitrile. Then, 5 mL of the obtained solution was taken up by a whole pipette, charged into a 50 mL measuring flask, and then diluted with acetonitrile to prepared a sample solution. The thus prepared sample solution was subjected to the respective analyses.

Example 1

[Step (1)]

In a nitrogen gas atmosphere, a 20 L separable flask equipped with a stirrer, a cooling tube and a thermometer was charged with 1737 g of acetic anhydride and 5 g of a boron trifluoride diethyl ether complex. While maintaining a liquid temperature of the obtained mixed solution in the range of from 0 to 20° C., 1073 g of methacrolein (purity: 94.7%) was added dropwise thereto, and the resulting mixture was stirred for 2 h. The mixture was mixed with 8184 g of 1,2-methylenedioxybenzene, and then 62 g of a boron trifluoride diethyl ether complex was added dropwise thereto, followed by stirring the resulting mixture at 40° C. for 3 h. After completion of the reaction, the resulting reaction mixture was washed with water to extract an organic layer therefrom. The thus extracted organic layer was carried out distillation to remove unreacted 1,2-methylenedioxybenzene therefrom, thereby obtaining a residue solution. The thus obtained residue solution in an amount of 3231 g was carried out distillation (179 to 190° C./3 to 5 torr) to obtain 2857 g of a crude product of 1-acetoxy-3-(3,4-methylenedioxyphenyl)-1-propene (purity: 94.9%) as a main fraction.

[Step (2)]

(Transesterification Reaction)

The thus obtained crude product was mixed with 3183 g of methanol and 24.1 g of potassium carbonate, and the resulting mixture was stirred at a temperature of from 35 to 55° C. for 2 h. After completion of the reaction, the obtained reaction solution was mixed with 22.6 g of a 85 wt % phosphoric acid aqueous solution, and the resulting mixture was stirred and then subjected to distillation under reduced pressure to remove unreacted methanol therefrom. The thus obtained reaction mixture was washed with water to obtain 2385 g of a crude product of 2-methyl-3-(3,4-methylenedioxyphenyl) propanal (purity: 93.0%).

(Distillative Purification)

Next, 722 g of the thus obtained crude product of 2-methyl-3-(3,4-methylenedioxyphenyl)propanal was subjected to distillative purification using a rectifier equipped with a 1 L flask (packing material: "SULZER PACKING EX"; φ25 mm×1100 mm in height). An initial fraction was distilled off from the crude product at a reflux ratio of 10 (139 to 152° C./6 torr) to obtain 183 g of a distillate as the initial fraction. Next, from the time at which the purity of 2-methyl-3-(3,4-methylenedioxyphenyl)propanal reached 98.5%, a main fraction was distilled off from the crude product at a reflux ratio of 1 (152 to 154° C./6 torr), thereby obtaining 440 g of 2-methyl-3-(3,4-methylenedioxyphenyl)propanal as an final product (purity: 99.6%). The content of 1-acetyl-3,4-methylenedioxybenzene in the thus obtained 2-methyl-3-(3,4-methylenedioxyphenyl)propanal was 150 ppm, and the content of acetic acid therein was 5 ppm.

The thus obtained final product was allowed to stand in air at room temperature (23 to 27° C.) and measured for a coloration degree (APHA index) and a purity with the lapse of time to examine a stability thereof under an ordinary life environmental conditions (using indoor light for daytime and light of fluorescent lamp for night). The results are shown in Table 1.

Example 2

The procedure of the step (1) through the transesterification reaction of the step (2) of Example 1 was carried out in the same manner as in Example 1, thereby obtaining 2330 g of a crude product of 2-methyl-3-(3,4-methylenedioxyphenyl) propanal (purity: 95.2%). 678 g of the obtained crude product was subjected to distillation at a reflux ratio of 8 (100 to 147° C./5 torr) to distil off 118 g of an initial fraction therefrom, and then subjected to distillation at a reflux ratio of 0.5 (148 to 149° C./5 torr) to distil off a main fraction therefrom, thereby obtaining 520 g of 2-methyl-3-(3,4-methylenedioxyphenyl) propanal as an final product (purity: 99.3%). The purity of 2-methyl-3-(3,4-methylenedioxyphenyl)propanal at the time of changeover between the initial fraction and the main fraction was 98.0%. The content of 1-acetyl-3,4-methylenedioxybenzene in the thus obtained final product was 330 ppm, and the content of acetic acid therein was 1 ppm or less. The coloration degree and stability of the thus obtained final product were examined in the same manner as in Example 1. The results are shown in Table 1.

Example 3

[Step (1)]

In a nitrogen gas atmosphere, a 20 L separable flask equipped with a stirrer, a cooling tube and a thermometer was charged with 1835 g of acetic anhydride and 4.3 g of a boron trifluoride diethyl ether complex. While maintaining a liquid temperature of the thus obtained mixed solution in the range of from 0 to 20° C., 1048 g of methacrolein (purity: 94.4%) was added dropwise thereto, and the resulting mixture was stirred for 2 h. The mixture was mixed with 8833 g of 1,2-methylenedioxybenzene, and then 52 g of a boron trifluoride diethyl ether complex was added dropwise thereto, and then stirred the resulting mixture at 40° C. for 3 h. After completion of the reaction, the resulting reaction mixture was washed with water to extract an organic layer therefrom. The thus extracted organic layer was subjected to distillation to remove unreacted 1,2-methylenedioxybenzene therefrom, thereby obtaining a residue solution. 3007 g of the obtained residue solution was subjected to distillation (174 to 185° C./3 to 4 torr) using a thin film evaporator to obtain 2660 g of a crude product of 1-acetoxy-3-(3,4-methylenedioxyphenyl)-1-propene (purity: 97.0%) as a main fraction.

[Step (2)]

(Transesterification Reaction)

The obtained crude product was mixed with 3220 g of methanol and 22.0 g of potassium carbonate, and the resulting mixture was stirred at a temperature of from 35 to 55° C. for 2 h. After completion of the reaction, the obtained reaction solution was mixed and stirred with 20.6 g of a 85 wt % phosphoric acid aqueous solution. The resulting mixture was carried out distillation under reduced pressure to remove unreacted methanol therefrom. The thus obtained reaction solution was washed with water to obtain 2167 g of a crude product of 2-methyl-3-(3,4-methylenedioxyphenyl)propanal (purity: 95.1%).

(Distillative Purification)

Next, 792 g of the obtained crude product of 2-methyl-3-(3,4-methylenedioxyphenyl)propanal was subjected to distillation using a rectifier equipped with a 1 L flask (packing material: "SULZER PACKING EX"; φ25 mm×1100 mm in height) at a reflux ratio of 10 (pressure: 7 to 15 torr; temperature: 109 to 157° C.) to extract 215 g of an initial fraction therefrom. Then, the crude product was subjected to distillation at a reflux ratio of 1 (156 to 157° C./7 torr) to distil off a main fraction therefrom, thereby obtaining 460 g of 2-methyl-3-(3,4-methylenedioxyphenyl)propanal as the main fraction, i.e., as an final product (purity: 99.7%). The purity of 2-methyl-3-(3,4-methylenedioxyphenyl)propanal at the time of changeover between the initial fraction and the main fraction was 98.5%. The content of 1-acetyl-3,4-methylenedioxybenzene in the thus obtained final product was 68 ppm, and the content of acetic acid therein was 6 ppm. Further, the coloration degree and stability of the thus obtained final product were examined in the same manner as in Example 1. The results are shown in Table 1.

Example 4

The procedure of the step (1) through the transesterification reaction of the step (2) of Example 1 was carried out in the same manner as in Example 1, thereby obtaining 2195 g of a crude product of 2-methyl-3-(3,4-methylenedioxyphenyl)propanal (purity: 96.1%). The thus obtained crude product in an amount of 630 g was subjected to distillative purification at a reflux ratio of 8 to distil off 59 g of an initial fraction therefrom, and then subjected to distillation at a reflux ratio of 0.5 to distil off a main fraction therefrom, thereby obtaining 58.3 g of 2-methyl-3-(3,4-methylenedioxyphenyl)propanal as the main fraction, i.e., as an final product (purity: 97.0%). The purity of 2-methyl-3-(3,4-methylenedioxyphenyl)propanal at the time of changeover between the initial fraction and the main fraction was 95.0%. The content of 1-acetyl-3,4-methylenedioxybenzene in the obtained final product was 2800 ppm, and the content of acetic acid therein was 3 ppm. The coloration degree and stability of the thus obtained final product were examined in the same manner as in Example 1. The results are shown in Table 1.

Example 5

The procedure of the step (1) through the transesterification reaction of the step (2) of Example 1 was carried out in the same manner as in Example 1, thereby obtaining 2-methyl-3-(3,4-methylenedioxyphenyl)propanal having a 1-acetyl-3,4-methylenedioxybenzene content below its lower detection limit and an acetic acid content of 1 ppm or less (as a distillate 3). The thus obtained fraction was mixed with 2500 ppm of 1-acetyl-3,4-methylenedioxybenzene to measure a coloration degree (APHA) and a purity thereof. The results are shown in Table 1.

Example 6

[Step (3)]

A 300 mL three-necked flask equipped with a stirrer and a thermometer was charged with 22.1 g of methacrolein (300 mmol; purity: 95.0%), 36.8 g (360 mmol) of acetic anhydride and 171.2 g (1410 mmol) of 1,2-methylenedioxybenzene, followed by mixing the contents of the flask with each other. While maintaining an inside temperature of the flask in the range of from 5 to 45° C., 0.97 g (6.0 mmol) of iron (III) chloride (anhydride) was slowly added to the resulting mixture, and stirred the mixture for 5 h. After completion of the reaction, the obtained reaction product was mixed with 200 mL of water, and stirred for 10 min. Next, after separating a water layer from the reaction mixture, the resulting organic layer was mixed again with 200 mL of water, and stirred for 10 min. After separating a water layer again, the resulting organic layer was subjected to distillation to remove unreacted 1,2-methylenedioxybenzene therefrom, thereby obtaining a residue solution. As a result of analysis the residue solution by HPLC, it was confirmed that a yield of 1-acetoxy-2-methyl-3-(3,4-methylenedioxyphenyl)-1-propene was 54.9 g (yield based on the amount of methacrolein used: 78.1%).

[Step (2)]

Next, the obtained crude product of 1-acetoxy-2-methyl-3-(3,4-methylenedioxyphenyl)-1-propene was subjected to the same distillation procedure as in the step (2) of Example 2 to distil off a main fraction therefrom, thereby obtaining 27.0 g of 2-methyl-3-(3,4-methylenedioxyphenyl)propanal as the main fraction, i.e., as an final product (purity: 99.1%). The content of 1-acetyl-3,4-methylenedioxybenzene in the thus obtained final product was 1150 ppm, and the content of acetic acid therein was 18 ppm. Further, the coloration degree and stability of the final product were examined in the same manner as in Example 1. The results are shown in Table 1.

Comparative Example 1

The procedure of the step (1) through the transesterification reaction of the step (2) of Example 1 was carried out in the same manner as in Example 1, thereby obtaining 2288 g of a crude product containing 2-methyl-3-(3,4-methylenedioxyphenyl)propanal (purity: 93.3%). 764 g of the obtained crude product out of its whole amount was carried out the distillative purification at a reflux ratio of 10 to distil off 263 g of an initial fraction therefrom, and then subjected to distillation at a reflux ratio of 1.0 to obtain 400 g of a main fraction (99.8%). The purity of 2-methyl-3-(3,4-methylenedioxyphenyl)propanal at the time of changeover between the initial fraction and the main fraction was 99.0%. The content of 1-acetyl-3,4-methylenedioxybenzene in the thus obtained main fraction was below the lower detection limit (10 ppm or less). Further, the coloration degree and stability of the thus obtained product were examined in the same manner as in Example 1. The results are shown in Table 1. The change in coloration degree of the product with the lapse of time was considerably large, and, therefore, it was not possible to keep a sufficient quality thereof.

Comparative Example 2

The procedure of the step (1) through the transesterification reaction of the step (2) of Example 2 was carried out in the same manner as in Example 2, thereby obtaining 2305 g of a crude product of 2-methyl-3-(3,4-methylenedioxyphenyl) propanal (purity: 95.3%). 619 g of the obtained crude product out of its whole amount was carried out distillative purification at a reflux ratio of 5 to distil off 59 g of an initial fraction therefrom, and then subjected to distillation at a reflux ratio of 0.5 to obtain 36.4 g of a main fraction (96.1%). The purity of 2-methyl-3-(3,4-methylenedioxyphenyl)propanal at the time of changeover between the initial fraction and the main fraction was 92.0%. The content of 1-acetyl-3,4-methylenedioxybenzene in the thus obtained main fraction was 3880 ppm. Further, the coloration degree and stability of the thus obtained product were examined in the same manner as in Example 1. The results are shown in Table 1. Although the change in coloration degree of the product with the lapse of time was small, it was not possible to attain a satisfactory fragrance.

Reference Example 1

A commercially available product of 2-methyl-3-(3,4-methylenedioxyphenyl)propanal produced via heliotropin from safrole as a raw material (available from ACROS ORGANICS Inc.; 95.60%) already exhibited a coloration degree APHA index of 300 or more when unpacked. The commercially available product contained no 1-acetyl-3,4-methylenedioxybenzene, but contained 2,6-di-tert-butyl-4-methyl phenol (BHT: antioxidant) in an amount of 1500 ppm (area percentage as measured by gas chromatography).

In addition, the 2-methyl-3-(3,4-methylenedioxyphenyl) propanal compositions obtained in the respective Examples and Comparative Examples were evaluated by a perfumer according to the following ratings. The results are shown in Table 1.

(Evaluation of Fragrance)

A: Fragrance without acid odor, and practically usable as a perfume.

B: Off-odor occurred, and practically unusable as a perfume. (Evaluation of Difference in Fragrance from Commercially Available Product (ACROS ORGANICS Inc.))

A: Fresher and clearer fragrance different from that of the commercially available product.

B: Similar fragrance to that of the commercially available product.

—: No evaluation was carried out.

TABLE 1

| | Examples | | | | | |
|---|---|---|---|---|---|---|
| | 1 | 2 | 3 | 4 | 5 | 6 |
| Compound 1*1 (ppm) | 150 | 330 | 68 | 2800 | 2500 | 1150 |
| BHT*2 (ppm) | 0 | 0 | 0 | 0 | 0 | 0 |
| Change in APHA index (elapsed time) | | | | | | |
| 0 h | 15 | 15 | 20 | 10 | 45 | 20 |
| 24 h | 50 | 25 | 50 | 10 | 40 | — |
| 48 h | 60 | 30 | 60 | 15 | 40 | — |
| 72 h | 60 | 35 | 70 | 15 | 40 | — |
| 198 h | 75 | 60 | 75 | 20 | 50 | — |
| 560 h | 80 | 65 | 80 | 30 | 70 | — |
| 704 h | 70 | 70 | 80 | 40 | 80 | 50 |
| Purity of HLF*3 (%) | | | | | | |
| 0 h | 99.6 | 99.3 | 99.7 | 97.0 | 99.7 | 99.1 |
| 704 h | 99.5 | 99.2 | 99.5 | 97.1 | 99.5 | 98.9 |
| Residual rate of HLF (%)*4 | 99.9 | 100.0 | 99.8 | 100.1 | 99.8 | 99.8 |
| Evaluation of fragrance | | | | | | |
| Fragrance | A | A | A | A | A | A |
| Difference*5 | A | A | A | A | A | A |

| | Comparative Examples | | |
|---|---|---|---|
| | 1 | 2 | Reference Example 1 |
| Compound 1*1 (ppm) | 0 | 3880 | Reagent |
| BHT*2 (ppm) | 0 | 0 | 1500 |
| Change in APHA index (elapsed time) | | | |
| 0 h | 20 | 10 | >300 |
| 24 h | 90 | 10 | |
| 48 h | 90 | 10 | |
| 72 h | 90 | 20 | |
| 198 h | 100 | 20 | |
| 560 h | 100 | 30 | |
| 704 h | 100 | 30 | |
| Purity of HLF*3 (%) | | | |
| 0 h | 99.8 | 96.1 | |
| 704 h | 99.4 | 96.0 | |
| Residual rate of HLF (%)*4 | 99.6 | 99.9 | |
| Evaluation of fragrance | | | |
| Fragrance | — | B | — |
| Difference*5 | — | — | — |

Note
*1: Compound 1: 1-acetyl-3,4-(methylenedioxy)benzene
*2: BHT: 2,6-di-t-butyl-4-methyl phenol
*3: HLF: 2-methyl-3-(3,4-methylenedioxyphenyl)propanal
*4: Residual rate of HLF (%) = [HLF purity (%; 704 h)/HLF purity (%; 0 h)] × 100 (%)
*5: Difference in fragrance from that of commercially available product.

INDUSTRIAL APPLICABILITY

2-Methyl-3-(3,4-methylenedioxyphenyl)propanal produced by the production processes of the present invention hardly suffers from undesirable coloration or decomposition, and exhibits a fresher and clearer fragrance different from those of the conventional compounds produced from safrole or heliotropin as a starting material, and is therefore useful as a component for perfumes and cosmetics.

The invention claimed is:

1. A method for keeping a quality of 2-methyl-3-(3,4-methylenedioxyphenyl)propanal, comprising:
   incorporating from 50 to 3000 ppm of 1-acetyl-3,4-methylenedioxybenzene in the 2-methyl-3-(3,4-methylenedioxyphenyl)propanal.

2. The method for keeping a quality of 2-methyl-3-(3,4-methylenedioxyphenyl)propanal according to claim 1, wherein the 2-methyl-3-(3,4-methylenedioxyphenyl)propanal is produced from 1-acetoxy-2-methyl-3-(3,4-methylenedioxyphenyl)-1-propene.

* * * * *